(12) United States Patent
Graham

(10) Patent No.: US 8,012,766 B2
(45) Date of Patent: Sep. 6, 2011

(54) PREDICTION OF ASPIRATED VOLUME OF A LIQUID

(75) Inventor: Edward J. Graham, Penfield, NY (US)

(73) Assignee: Ortho-Clinical Diagnostics, Inc., Rochester, NY (US)

(*) Notice: Subject to any disclaimer, the term of this patent is extended or adjusted under 35 U.S.C. 154(b) by 949 days.

(21) Appl. No.: 11/194,817

(22) Filed: Aug. 1, 2005

(65) Prior Publication Data

US 2007/0026534 A1 Feb. 1, 2007

(51) Int. Cl.
*G01N 1/10* (2006.01)

(52) U.S. Cl. .......... 436/180; 436/43; 436/54; 73/864.11

(58) Field of Classification Search .................. 436/180, 436/54, 43, 99; 422/63, 100, 64, 500–501; 73/864.11

See application file for complete search history.

(56) References Cited

U.S. PATENT DOCUMENTS

| | | | |
|---|---|---|---|
| 4,496,293 A | 1/1985 | Nakamura et al. |
| 4,743,561 A | 5/1988 | Shaffar |
| 5,499,545 A | 3/1996 | Kimura et al. |
| 5,885,530 A | 3/1999 | Babson et al. |
| 5,927,547 A | 7/1999 | Papen et al. |
| 6,060,320 A | 5/2000 | Dorenkott et al. |
| 6,079,283 A | 6/2000 | Papen et al. |
| 6,083,762 A | 7/2000 | Papen et al. |
| 6,094,966 A | 8/2000 | Papen et al. |
| 6,112,605 A | 9/2000 | Papen et al. |
| 6,121,049 A | 9/2000 | Dorenkott et al. |
| 6,203,759 B1 | 3/2001 | Pelc et al. |
| 6,220,075 B1 | 4/2001 | Papen et al. |
| 6,422,431 B2 | 7/2002 | Pelc et al. |
| 6,797,518 B1 | 9/2004 | Jacobs et al. |
| 7,250,303 B2 | 7/2007 | Jakubowicz et al. |
| 2003/0022380 A1* | 1/2003 | Jakubowicz et al. ........... 436/54 |
| 2005/0234673 A1 | 10/2005 | Saitoh et al. |
| 2006/0090576 A1 | 5/2006 | Sander |

FOREIGN PATENT DOCUMENTS

| | | |
|---|---|---|
| EP | 0215534 | 3/1987 |
| EP | 1209471 | 5/2002 |
| WO | WO 01/88549 | 11/2001 |

* cited by examiner

*Primary Examiner* — Brian R Gordon
(74) *Attorney, Agent, or Firm* — Todd J. Burns

(57) ABSTRACT

Aspirating a liquid, includes: providing an aspirating probe comprising probe tip and piston pump, wherein the probe tip and piston pump are in fluid communication; measuring an initial gas pressure in the probe prior to liquid entering the liquid being aspirated; moving the tip into the liquid; moving the piston a distance corresponding to the volume of liquid being aspirated; measuring gas pressure in the volume of gas when the piston stops moving and the liquid pulled into the tip has equilibrated; determining piston volume created by movement of the piston; and determining volume of liquid aspirated by the following formula: $V_{liquid\ aspirated} = V_{piston\ volume} - ((P_{initial} - P_{final}) * \text{Volume/unit pressure})$, wherein $P_{initial}$ is initial gas pressure before liquid enters the tip, $P_{final}$ is the final pressure of volume of gas after the liquid has equilibrated, and Volume/unit pressure is the change of gas volume for each change of unit pressure.

18 Claims, 3 Drawing Sheets

PREDICTION OF ASPIRATED VOLUME OF A LIQUID

BACKGROUND OF THE INVENTION

The present invention relates to predicting the amount of an aspirated liquid, particularly an aspirated sample used in a diagnostic analyzer.

Known diagnostic analyzers include immunodiagnostic and clinical chemistry analyzers such as the VITROS® ECi immunodiagnostic analyzer, or a clinical chemistry analyzer such as the VITROS® 5,1 FS, both sold by Ortho-Clinical Diagnostics, Inc. All such analyzers are collectively called diagnostic analyzers. Such systems rely on a constant sample volume being delivered to the reaction to give a precise reported assay result. The precision of the sample aspiration is typically known and is often a significant contributor to the precision of reported results. These diagnostic analyzers commonly use pressure detection systems to monitor the aspiration of sample and reagent liquids. The recorded pressure profile is monitored and evaluated in an attempt to determine if foam, bubbles, clots or any other anomaly is observed which could adversely affect the intended aspirate or dispense volume. When a problem is detected, the instrument will alert the operator, and suppress the result. While detecting errors and discarding the results will improve assay precision, it will reduce usable results, resulting in the use of more sample to re-run the analysis.

In an attempt to conserve sample volume, especially in pediatric and geriatric settings, and in an attempt to minimize reagent usage for cost consideration, test volumes are under constant pressure to be reduced. As volumes are reduced below 5 uL, liquid handling system requirements for precision and accuracy are becoming more stringent. Small deviations in delivered volume of liquid have a direct affect on the reaction and result. Some patents describe the art of detecting liquid handling anomalies such as bubbles, clots and foam as well as predicting that an aspirated volume is insufficient to allow reporting of a result. See, e.g., U.S. Pat. No. 6,060,320. U.S. Pat. No. 6,112,605 discloses aspirating microvolumes of a transfer liquid. An air gap is located between the transfer liquid and the system liquid. After a dispense of transfer liquid, the transfer liquid will return to its prior position due to capillary forces. This causes the air gap volume to increase along with a corresponding decrease in pressure. Based on the decrease in pressure of the air gap, the volume of liquid dispensed can be determined. U.S. Pat. Nos. 6,422,431, 6,083,762, 6,220,075, 6,094,966, 5,927,547, 6,079,283 and 6,203,759 all disclose aspirating and/or dispensing liquids using an aspirate/dispense probe. However, none of the known art teaches correcting for small volume errors in aspiration caused by conditions such as viscosity.

For the foregoing reasons, there is a need for a method of aspirating a liquid that can correct for variations in the volume of an aspirated liquid, and hence, more accurately predict the actual volume of aspirated liquid.

SUMMARY OF THE INVENTION

The present invention is directed to a method that solves the foregoing problems of the inability to correct for volumetric errors in an aspirating process, particularly in a diagnostic analyzer.

One aspect of the invention is directed to a method of aspirating a liquid. The method includes: providing an aspirating probe which comprises a probe tip and a piston pump, wherein the probe tip and piston pump are in fluid communication; measuring an initial gas pressure in the tip of the aspirating probe prior to the tip entering the liquid to be aspirated; moving the tip into the liquid, whereby a volume of gas is located between the top of the liquid and the piston of the piston pump; moving the piston of the piston pump a predetermined distance which corresponds to a selected volume of liquid to be aspirated, whereby a column of liquid is aspirated into the tip; measuring the gas pressure in the volume of gas when the piston stops moving and the column of liquid aspirated into the tip has equilibrated; determining the piston volume created by the movement of the piston; and determining the volume of the column of liquid aspirated by the following formula:

$$V_{liquid\ aspirated} = V_{piston\ volume} - ((P_{A/Dinitial} - P_{A/Dfinal}) * Volume/ADC),$$

wherein $P_{A/Dinitial}$ is initial gas pressure in ADC before the liquid enters the tip, $P_{A/Dfinal}$ is final pressure of the volume of gas in ADC, ADC is pressure as expressed in analog/digital counts; and Volume/ADC is the change in the volume of the gas per unit ADC.

According to another aspect of the invention, there has been provided a method of aspirating a liquid, comprising: providing an aspirating probe which comprises a probe tip and a piston pump, wherein the probe tip and piston pump are in fluid communication; measuring an initial gas pressure in the tip of the aspirating probe prior to the tip entering the liquid to be aspirated; moving the tip into the liquid, whereby a volume of gas is located between the top of the liquid and the piston of the piston pump; moving the piston of the piston pump a predetermined distance which corresponds to a selected volume of liquid to be aspirated, whereby a column of liquid is aspirated into the tip; measuring the gas pressure in the volume of gas when the piston stops moving and the column of liquid aspirated into the tip has equilibrated; determining the piston volume created by the movement of the piston; and determining the volume of the column of liquid aspirated by the following formula:

$$V_{liquid\ aspirated} = V_{piston\ volume} - ((P_{initial} - P_{final}) * Volume/unit\ pressure),$$

wherein $P_{initial}$ is initial gas pressure before the liquid enters the tip, $P_{final}$ is final pressure of the volume of gas after the column of liquid has equilibrated, and Volume/unit pressure is the change of the gas volume for each change of unit pressure.

According to yet another aspect of the invention, there has been provided a method of analyzing a sample for an analyte. The method includes: providing a source of a sample; providing an aspirating probe which comprises a probe tip and a piston pump, wherein the probe tip and piston pump are in fluid communication; measuring an initial air pressure in the tip of the aspirating probe prior to the tip entering the liquid to be aspirated; moving the tip into the sample, whereby a volume of air is located between the top of the liquid and the piston of the piston pump; moving the piston of the piston pump a predetermined distance which corresponds to a selected volume of liquid to be aspirated, whereby a column of liquid is aspirated into the tip; measuring the air pressure in the volume of air when the piston stops moving and the column of sample pulled aspirated into the tip has equilibrated; determining the piston volume created by the movement of the piston; and determining the volume of the column of sample aspirated by the following formula:

$$V_{liquid\ aspirated} = V_{piston\ volume} - ((P_{A/Dinitial} - P_{A/Dfinal}) * Volume/ADC),$$

wherein $P_{A/Dinitial}$ is initial air pressure before the sample enters the tip, $P_{A/Dfinal}$ is final pressure of the volume of air after the column of liquid has equilibrated, ADC is pressure as expressed in analog/digital counts; and Volume/ADC is the change in the volume of the gas per unit ADC;

dispensing the sample into a sample holder;

optionally dispensing a reagent into the sample holder; performing a measurement on the sample; and determining a concentration of analyte in the sample based on the measurement and the determined volume of the column of sample.

Further objects, features and advantages of the present invention will be apparent to those skilled in the art from detailed consideration of the preferred embodiments that follow.

DETAILED DESCRIPTION OF PREFERRED EMBODIMENTS

The present invention provides the ability to use a pressure detection system, preferably a high-resolution pressure detection system in a diagnostic analyzer to give a more correct determination of aspirated volume. The ability to more correctly determine the liquid volume, which liquid is used in a subsequent operations such as a reaction, and utilize the corrected volume as a factor in computing the final result reduces the systems dependence on precision of the metering system while improving the overall assay precision of the system. That is, overall assay precision is not as dependent on obtaining aspirate precision, because the present invention will correct for errors in the aspirate process. The present invention is in contrast to simply detecting that the delivered volume is discrepant and suppressing the result. The present invention also reduces the effects from liquid rheologies that are very difficult to detect and to compensate for. The impact of this is an improvement in the baseline assay precision of the system without the issue of frequent repeats for samples that are discarded when incorrect volumes are detected. In previous detection systems only substantial outliers were removed since attempting to improve baseline assay precision with detection will result in a large percentage of the usable results being discarded. As used herein "correctly" or "correct" means determining the calculated volume of liquid aspirated to within 5% of the actual volume aspirated as determined by gravimetry, more preferably 2% and more preferably <1%.

Figure 1:
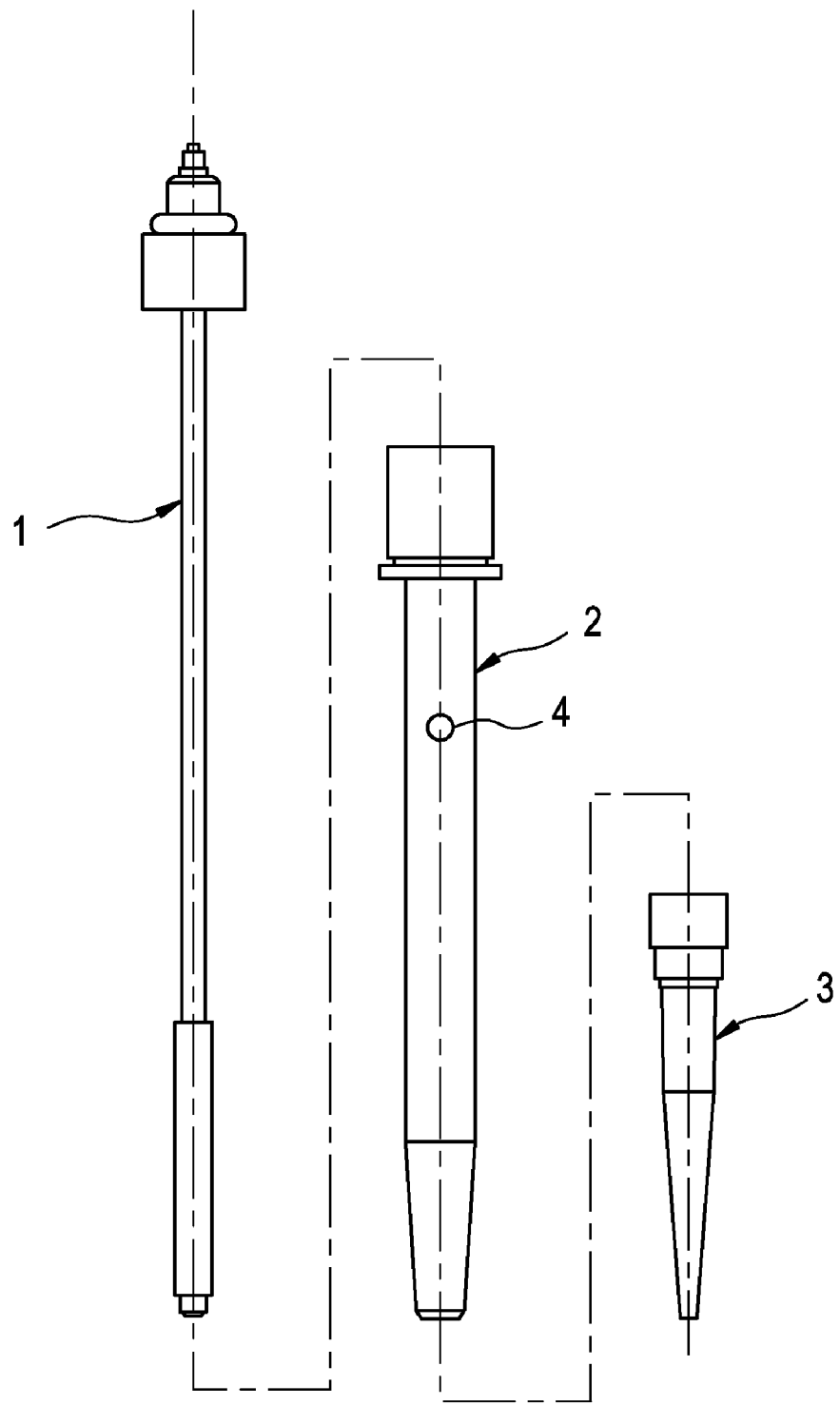
FIG. 1 is a side schematic view of an aspirating probe and probe tip shown in a disassembled state.

As shown in FIG. 1, a preferred embodiment shows an aspirate/dispense system which utilizes a pump that includes piston 1 inside a precision molded sleeve 2. The sleeve 2 also acts to accept press fit tips 3, preferably disposable tips that will carry the liquid, such as either a sample, reagent or wash liquid. A stepper motor (not shown) moves the piston to cause piston displacement in the sleeve. The displacement creates positive and negative pressures in the disposable tip that result in liquid displacement within the tip. Air pressure above the liquid column of sample or reagent in the tip 3 is monitored by a pressure transducer (not shown) via a clearance hole 4 through the center of the piston. These piston pumps are also known in the art as a syringe pump. Throughout this disclosure, both terms are used interchangeably.

The present invention utilizes Boyle's law which describes the relationship between volume and pressure as it relates to a gas, assuming temperature is constant. In the system described in FIG. 1, a Boyle's law one to one relationship would exist between pump displacement and liquid movement in the disposable tip, if the liquid, e.g., sample, reagent or wash fluid, acted as a gas. However, liquids do not follow the Boyle's law one-to-one relationship for a number of reasons such as viscosity and surface tension of the liquid being transported, as well as interactions between the disposable tip material and the liquid, which may influence liquid movement into or out of the tip. However, the gas column, e.g. air column, being monitored above the liquid column does follow Boyle's law. Since the system volume, i.e., that part of the system between the piston and tip end, can only be occupied by gas or liquid, the liquid volume can be determined if the air volume is determinable. For example, if the pressure prior to the tip entering the liquid, e.g., the liquid to be aspirated, is different than the pressure observed after leaving the liquid, there must be also be a change in the volume of the gas, e.g., air above the liquid. Taking the actual piston displacement and adjusting by the volume change in the air column above, results in the volume of liquid that is aspirated into the tip.

Thus, to determine the final volume of air after aspiration, the initial and final pressure must be known. In a preferred system described above, the pressure is measured in analog/digital counts (ADC) and the resolution of the pressure transducer is determined by measuring the response to piston displacement, with a disposable tip in place and moving the piston while the system is closed, (tip is plugged). That is, the pump is displaced a known volume using techniques described below. Using the known volume displaced and counting the number of ADCs, each ADC will correspond to a known change in volume, e.g., ADC/uL of pump displacement ($\Delta$pressure/$\Delta$volume). This calibration technique also serves to calibrate each system thus eliminating instrument-to-instrument variability due to combinations of transducer and pump differences, environmental effects (e.g., altitude), etc. While this description has been in terms of ADCs, other pressure units are also within the scope of the invention such as pascals, etc.

The volume created by moving the piston in the sleeve of the aspirate probe can be determined by a volume displaced per the amount of displacement created by the pump. In a preferred embodiment, the pump is a piston or syringe pump and the piston will move an incremental distance or step which is known using electronics well known in the art. The volume of each incremental move can be determined according to methods well known in the art and is based on the known distance the piston moves (i.e., distance per step times the number of steps) and the known geometry of the piston sleeve. For each incremental move, a digital or analog count is performed using electronics known in the aspirating art. By counting the number of counts, the total distance the piston moves and hence the volume the moving piston creates will be known.

Since the volume the moving piston creates ($V_{piston\ displaced}$), the initial ($P_{initial}$) and final pressures ($P_{final}$), and the volume of air displaced per unit pressure are known, an amount of liquid aspirated can be determined (i.e., predicted) according to the equation:

$$V_{liquid\ aspirated} = V_{piston\ volume} - ((P_{initial} - P_{final}) * \text{Volume/unit pressure}) \quad (1)$$

In terms of the preferred pressure unit ADC, since the volume the moving piston creates ($V_{piston\ displaced}$), the initial ($P_{A/Dinitial}$) and final pressures ($P_{A/Dfinal}$), in ADC, and the volume of air displaced per unit ADC are known, an amount of liquid aspirated can be determined (i.e., predicted) according to the equation:

$$V_{actual} = V_{piston\ displaced} - ((P_{A/Dinitial} - P_{A/Dfinal}) * \text{Volume per } ADC) \quad (2)$$

The liquid that is aspirated into the disposable tip can include any liquid capable of being aspirated. In diagnostic analyzer embodiments, the liquids will preferably be sample, reagents, wash fluids calibrator or control fluids. Samples can include body fluid such as whole blood, plasma, serum, urine or saliva, which may or may not have been pre-treated.

The gas that forms the gas column above the liquid will generally be air and the starting pressure will be ambient atmospheric pressure. However, in some embodiments, e.g., a gas tight sealed system, the gas may be something other than air, e.g. nitrogen or carbon dioxide, and the starting pressure may be a pressure other than atmospheric.

To aspirate a liquid, an aspirating probe such as that described above, preferably having a disposable tip is provided to aspirate the liquid. An initial pressure measurement ($P_{initial}$, preferably $P_{A/Dinitial}$) is taken before the probe tip is moved to a position just below the surface of the liquid. Once the probe tip is moved to a position in the liquid, an air column will be formed between the liquid to be aspirated and the piston of the pump. The piston is then moved a determined distance corresponding to the selected amount of liquid to be aspirated in a direction that will aspirate the liquid into the tip. At the end of piston travel, the aspirating probe is slowly moved out of the liquid. At this time, the final pressure ($P_{final}$, preferably $P_{A/Dfinal}$) is measured, preferably after the tip is removed from the liquid. The actual amount of liquid aspirated can then be determined according to equations (1) or (2) above.

In a preferred embodiment, the pressure is measured and recorded throughout the aspiration process. This is useful in determining whether the flow of liquid has been interrupted due to events such as aspiration of a bubble or clot and to determine when the tip is removed from the liquid to measure $P_{final}$, preferably $P_{A/Dfinal}$. If a bubble or clot is detected, the aspirated liquid, and any subsequent result generated, may be discarded or a further correction may be made. Depending on the total aspirated volume of liquid, compensation to the predicted volume may also be advantageous to account for liquid column height and surface tension effects to further improve on the accuracy of predicting the amount of liquid aspirated. For example, the weight of the fluid also creates a slight vacuum in the tip, the taller the column, the greater the vacuum; the meniscus force of high surface tension fluids can cause the fluid column to rise slightly in the tip, leaving a very small air column at the end of the tip which would contribute to error in the estimation of the volume and hence would benefit from correction.

In a preferred embodiment, the aspirating probe is part of an automated diagnostic analyzer and the aspirating process described above is part of a method for analyzing a sample for analyte. Automated diagnostic analyzers are a fixture in the clinical laboratory. The range of analyzers and methodologies in use is large. Some examples include spectrophotometric absorbance assay such as end-point reaction analysis and rate of reaction analysis, turbidimetric assays, nephelometric assays, radiative energy attenuation assays (such as those described in U.S. Pat. Nos. 4,496,293 and 4,743,561), ion capture assays, colorimetric assays, fluorometric assays, electrochemical detection systems, potentiometric detection systems, and immunoassays. Some or all of these techniques can be done with classic wet chemistries which utilize a cuvette; ion-specific electrode analysis (ISE); thin film formatted "dry" slide chemistries; bead and tube formats or microtiter plates; and the use of magnetic particles. U.S. Pat. No. 5,885,530 provides a description useful for understanding the operation of a typical automated analyzer for conducting immunoassays in a bead and tube format and is incorporated herein by reference.

In an operation of a typical diagnostic analyzer, sample is aspirated as described above. The sample is then dispensed in a sample holder. The sample holder can include those known in the art as described above. Dry slides, cuvettes and streptavidin coated wells are particularly preferred. A particularly preferred application of the present invention is to aspirate a sample liquid from a larger metering tip that has been previously sealed at the bottom, while sample is present in the tip. These type of sealed tips are called a CUVETIPT™ sold by Ortho-Clinical Diagnostics, Inc. and are described for example in U.S. Pat. No. 6,797,518 and in U.S. Published Patent Application No. 2003-0022380 A1 published Jan. 30, 2003, both of which are incorporated by reference in their entireties. Depending on the system being utilized various reagents may be added. The sample with reagents may be incubated for a selected amount of time, and then a measurement taken. For example, in chemistry analyzers the analysis can be a colorimetric analysis that utilizes a photometer operating at a specific wavelength. In immunoassays, the analysis can be made by chemiluminesence with the emitted light being measured by a luminometer. Such measurement systems, per se, are well known in the art.

Figure 2:
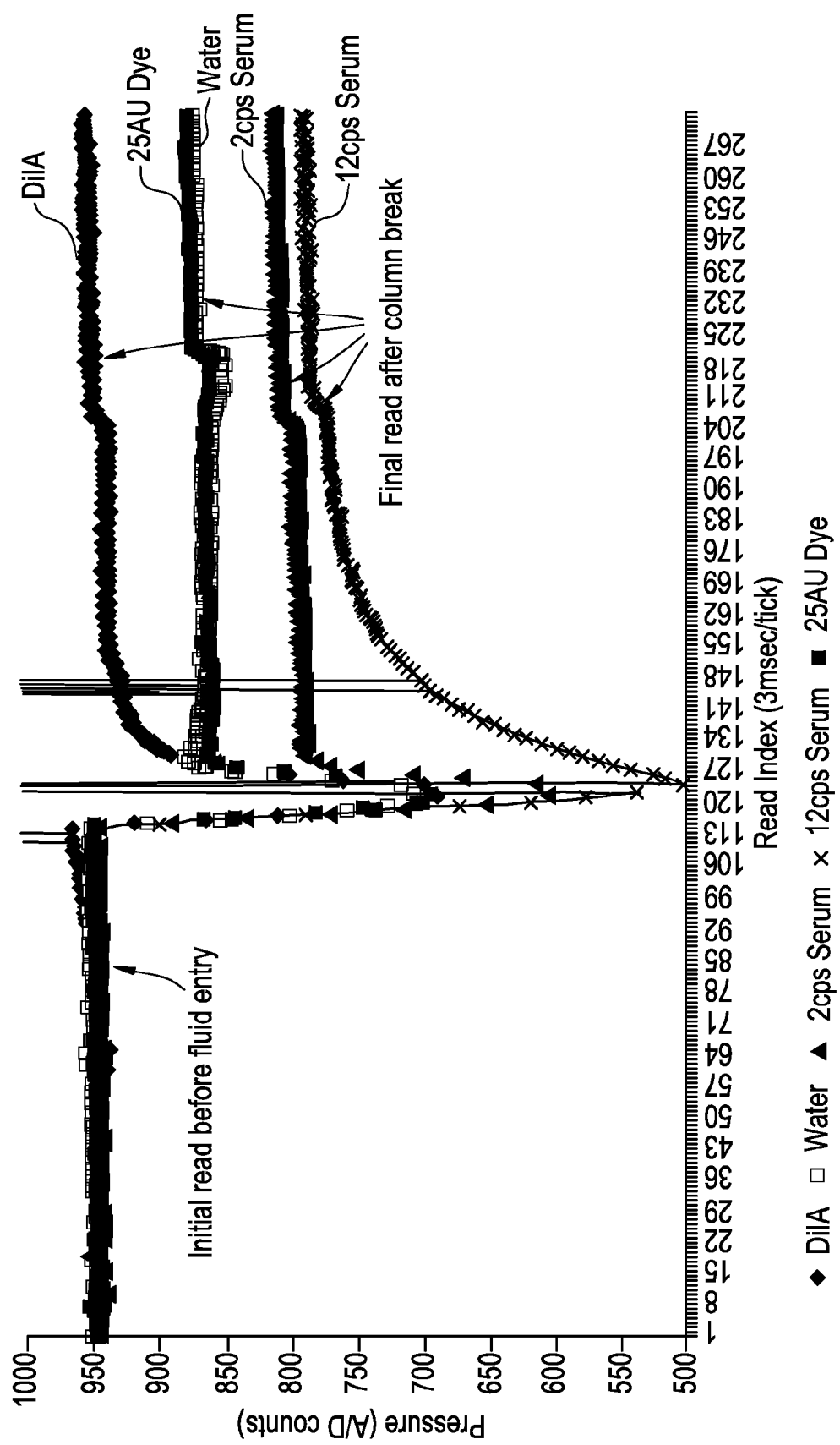
FIG. 2 is a pressure profile during an aspirate process for several different liquids.

Since the actual amount of aspirated sample will be known, the precision of the reported results can be improved, by either adjusting the amount of reactants added or adjusting the reported result by a factor that is determined by the difference between the actual amount of sample aspirated and the amount desired Now reference will be made to the non-limiting embodiments described in connection with the figures. FIG. 2 illustrates 2 uL aspiration pressure traces of five different liquids with varying degrees of surface tension and viscosity. The liquids are a diluent (♦), water (■), serum having a viscosity of 2 cps (▲) and serum having a viscosity of 12 cps (X) and a 25 AU dye (*). The points where the initial and final pressure reads would be taken are specified in FIG. 2. An initial reading is taken before the tip enters the liquid and a final reading immediately following the column break as the tip leaves the liquid.

Table 1 below shows gravimetric and predicted or corrected volume data for four liquid types, the target volume being 2 uL. As Table 1 confirms the predicted volume is much closer to the gravimetric value than the gravimetric value is to the selected target of 2 uL. This means the predicted or corrected volume correlates very well with the actual amount of liquid aspirated as determined by weighing the aspirated liquid (i.e., the gravimetric value). The "DeltaP" in Table 1 is the difference between the initial pressure and final pressure as described above.

TABLE 1

| | 2 cps Serum | | | | 12 cps Serum | | | | Diluent A (low surface tension) | | | | Water | | | |
|---|---|---|---|---|---|---|---|---|---|---|---|---|---|---|---|---|
| | Grav | DeltaP | Predicted Volume | Bias Actual vs Prediction | Grav | DeltaP | Predicted Volume | Bias Actual vs Prediction | Grav | DeltaP | Predicted Volume | Bias Actual vs Prediction | Grav | DeltaP | Predicted Volume | Bias Actual vs Prediction |
| | 1.97 | 131 | 1.9881 | 0.01 | 1.91 | 151 | 1.8901 | −0.02 | 2.64 | −9 | 2.6741 | 0.03 | 2.18 | 66 | 2.3066 | 0.13 |
| | 1.93 | 138 | 1.9538 | 0.02 | 1.84 | 165 | 1.8215 | −0.02 | 2.65 | −7 | 2.6643 | 0.01 | 2.15 | 74 | 2.2674 | 0.12 |
| | 1.94 | 137 | 1.9587 | 0.01 | 1.81 | 171 | 1.7921 | −0.02 | 2.63 | −3 | 2.6447 | 0.01 | 2.16 | 77 | 2.2527 | 0.09 |
| | 1.92 | 140 | 1.944 | 0.02 | 1.83 | 164 | 1.8264 | 0.00 | 2.68 | −8 | 2.6692 | −0.01 | 2.14 | 78 | 2.2478 | 0.11 |
| | 1.91 | 145 | 1.9195 | 0.01 | 1.77 | 172 | 1.7872 | 0.01 | 2.65 | −4 | 2.6496 | 0.00 | 2.14 | 79 | 2.2429 | 0.10 |
| | 1.92 | 142 | 1.9342 | 0.01 | 1.81 | 170 | 1.797 | −0.01 | 2.68 | −5 | 2.6545 | −0.02 | 2.18 | 79 | 2.2429 | 0.06 |
| | 1.89 | 143 | 1.9293 | 0.03 | 1.79 | 170 | 1.797 | 0.00 | 2.70 | −6 | 2.6594 | −0.04 | 2.17 | 76 | 2.2576 | 0.09 |
| | 189 | 143 | 1.9293 | 0.03 | 1.80 | 171 | 1.7921 | −0.01 | 2.65 | −5 | 2.6545 | 0.00 | 2.15 | 82 | 2.2282 | 0.08 |
| | 1.86 | 150 | 1.895 | 0.04 | 1.78 | 175 | 1.7725 | −0.01 | 2.64 | −4 | 2.6496 | 0.01 | 2.17 | 72 | 2.2772 | 0.11 |
| | 189 | 143 | 1.9293 | 0.03 | 1.76 | 177 | 1.7627 | 0.00 | 2.72 | −5 | 2.6545 | −0.06 | 2.25 | 70 | 2.287 | 0.04 |
| | 1.88 | 144 | 1.9244 | 0.04 | 1.78 | 175 | 1.7725 | −0.01 | 2.64 | −3 | 2.6447 | 0.00 | 2.15 | 82 | 2.2282 | 0.08 |
| | 1.88 | 141 | 1.9391 | 0.05 | 1.77 | 176 | 1.7676 | −0.01 | 2.67 | −5 | 2.6545 | −0.02 | 2.14 | 73 | 2.2723 | 0.13 |
| | 1.84 | 154 | 1.8754 | 0.04 | 1.76 | 173 | 1.7823 | 0.02 | 2.63 | −2 | 2.6398 | 0.01 | 2.13 | 78 | 2.2478 | 0.12 |
| | 1.88 | 146 | 1.9146 | 0.03 | 1.79 | 173 | 1.7823 | −0.01 | 2.63 | −6 | 2.6594 | 0.03 | 2.12 | 83 | 2.2233 | 0.10 |
| | 1.89 | 142 | 1.9342 | 0.04 | 1.77 | 173 | 1.7823 | 0.01 | 2.64 | −8 | 2.6692 | 0.03 | 2.16 | 79 | 2.2429 | 0.08 |
| | 1.97 | 149 | 1.8999 | 0.03 | 1.79 | 172 | 1.7872 | −0.01 | 2.64 | −5 | 2.6545 | 0.01 | 2.11 | 91 | 2.1841 | 0.07 |
| Mean | 1.89 | | 1.93 | 0.03 | 1.79 | | 1.79 | 0.00 | 2.66 | | 2.66 | 0.00 | 2.16 | | 2.25 | 0.09 |

A relationship between sample volume and reported assay results exists and when actual sample volume is known, the contribution to reported assay results precision from the metering system can be eliminated and replaced by the precision of the volume prediction. That is, there is a direct relationship between sample volume and assay precision. Factoring in the predicted volume delivered to a reaction allows compensation of the result to account for sample volume deviations, thus resulting in a more precise assay result. For example if the sample volume is low by 5%, the uncorrected assay result should be 5% low. To correct, divide the uncorrected assay result by 95% to give final result.

Figure 3:
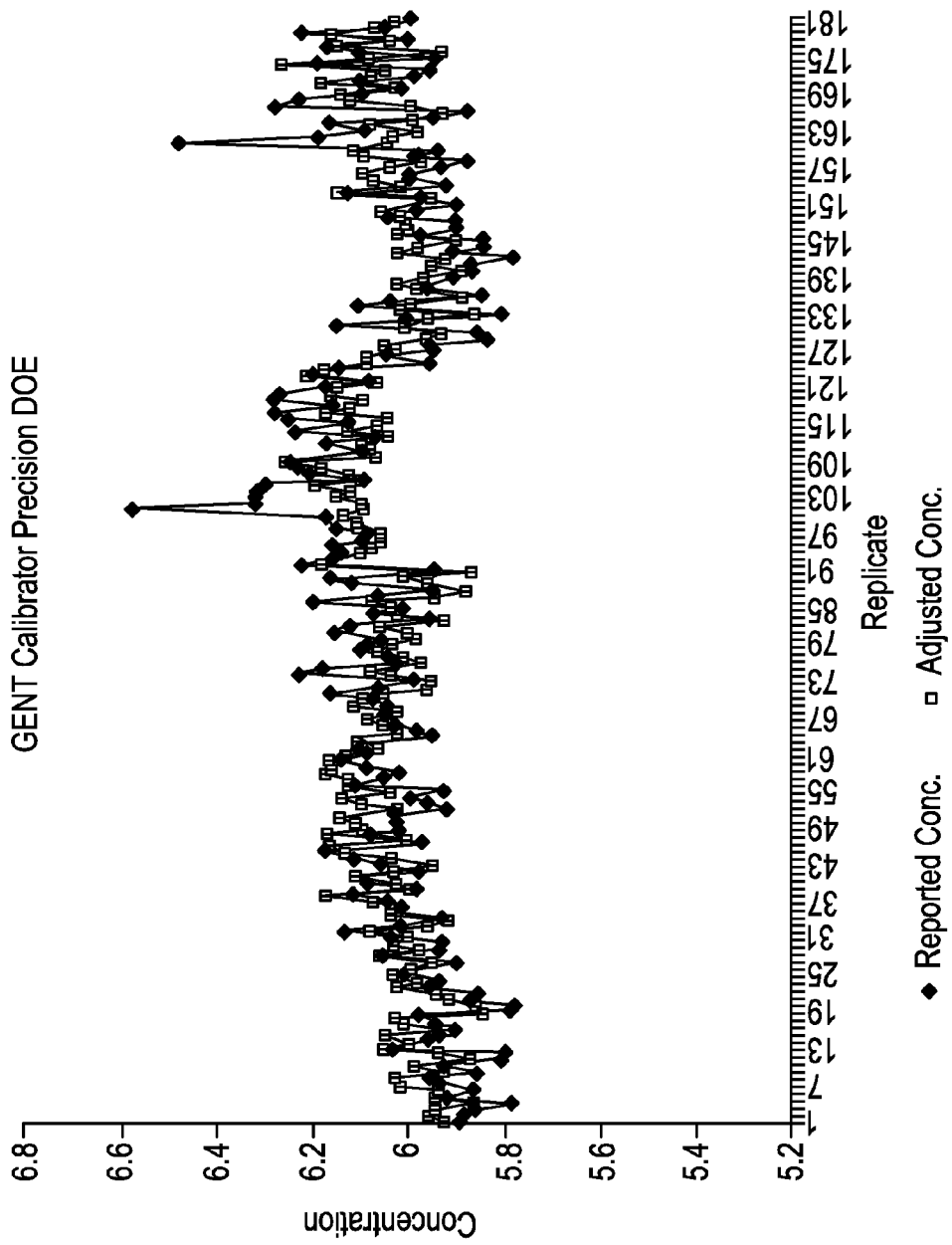
FIG. 3 is a graphical representation showing the concentration results of a single Gentimiacin precision run using both corrected and uncorrected aspirate volumes.

FIG. 3 shows reported results for a series of Gentamiacin tests all run with the same control fluid. The plotted data points in FIG. 3 are the reported concentration shown as (♦) in FIG. 3 from the analyzer and the concentration following the employment of volume correction described herein shown as (■) in FIG. 3. The y-axis shows concentration ug/mL and the x-axis shows the repetition number. The uncorrected precision for these results is 2.21% CV. The corrected run performed at 1.38% CV, a significant precision improvement. Note from FIG. 3 how the correction pulls the "outlier" points back into the normal population.

The method of predicting or correcting the volume of an aspirated liquid according to the present invention can be implemented by a computer program, having computer readable program code, interfacing with the computer controller of the analyzer as is known in the art.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

I claim:

1. A method of aspirating a liquid, comprising:
    providing an aspirating probe which comprises a probe tip and a piston pump, wherein the probe tip and piston pump are in fluid communication;
    measuring an initial gas pressure ($P_{A/Dinitial}$) in the tip of the aspirating probe prior to the tip entering the liquid to be aspirated;
    moving the tip into the liquid, whereby a volume of gas is located between the top of the liquid and the piston of the piston pump;
    moving the piston of the piston pump a predetermined distance which corresponds to a selected volume of liquid to be aspirated, whereby a column of liquid is aspirated into the tip;
    measuring the gas pressure in the volume of gas when the piston stops moving and the column of liquid aspirated into the tip has equilibrated ($P_{A/Dfinal}$);
    obtaining Volume/ADC, wherein ADC is pressure as expressed in analog/digital counts and Volume/ADC is the change in the volume of the gas per unit ADC;
    determining the piston volume created by the movement of the piston; and after aspiration determining the volume of the column of liquid aspirated by the following formula:

$$V_{liquid\ aspirated} = V_{piston\ volume} - ((P_{A/Dinitial} - P_{A/Dfinal}) * Volume/ADC),$$

wherein
    $P_{A/Dinitial}$ is initial gas pressure in ADC before the liquid enters the tip, and $P_{A/Dfinal}$ is final pressure of the volume of gas in ADC.

2. A method as claimed in claim 1, wherein the final pressure of the gas is measured after the column of liquid has equilibrated.

3. A method as claimed in claim 1, further comprising determining a gravimetric value of the liquid aspirated for the selected volume, wherein the determined volume of the column of liquid is closer to the determined gravimetric value than the selected volume.

4. A method as claimed in claim 1, wherein the gas is air.

5. A method as claimed in claim 1, wherein $V_{piston\ volume}$ is determined by the distance the piston travels during the aspirate process and the cross section of the piston.

6. A method as claimed in claim 5, wherein the piston travels in pump motor steps and the distance the piston traveled is determined by the number of pump motor steps.

7. A method as claimed in claim 1, wherein $P_{A/Dfinal}$ is measured after the aspirate probe tip has exited the liquid.

8. A method as claimed in claim 1, further comprising continuously monitoring the pressure during the aspirate process to determine whether there are any interruptions of flow of liquid into the probe tip.

9. A method as claimed in claim 8, wherein the interruptions are caused by one or more of bubbles or clots.

10. A method as claimed in claim 1, wherein the liquid is a sample of bodily fluid.

11. A method as claimed in claim 10, wherein the bodily fluid is one or more of whole blood, plasma, serum, urine or saliva.

12. A method as claimed in claim 1, wherein the liquid is one or more of a reagent, wash fluid, calibrator fluid or control fluid.

13. A method of aspirating a liquid, comprising:
   providing an aspirating probe which comprises a probe tip and a piston pump, wherein the probe tip and piston pump are in fluid communication;
   measuring an initial gas pressure ($P_{A/Dinitial}$) in the tip of the aspirating probe prior to the tip entering the liquid to be aspirated;
   moving the tip into the liquid, whereby a volume of gas is located between the top of the liquid and the piston of the piston pump;
   moving the piston of the piston pump a predetermined distance which corresponds to a selected volume of liquid to be aspirated, whereby a column of liquid is aspirated into the tip;
   measuring the gas pressure in the volume of gas when the piston stops moving and the column of liquid aspirated into the tip has equilibrated ($P_{A/Dfinal}$);
   obtaining Volume/unit pressure, wherein Volume/unit pressure is the change of the gas volume for each change of unit pressure;
   determining the piston volume created by the movement of the piston; and after aspiration determining the volume of the column of liquid aspirated by the following formula:

$$V_{liquid\ aspirated} = V_{piston\ volume} - ((P_{initial} - P_{final}) * \text{Volume}/\text{unit pressure}),$$

wherein
   $P_{initial}$ is initial gas pressure before the liquid enters the tip,
   $P_{final}$ is final pressure of the volume of gas after the column of liquid has equilibrated.

14. A method as claimed in claim 13, wherein the pressure is pascals.

15. A method of analyzing a sample for an analyte, comprising:
   providing a source of a sample;
   providing an aspirating probe which comprises a probe tip and a piston pump, wherein the probe tip and piston pump are in fluid communication;
   measuring an initial air pressure ($P_{A/Dinitial}$) in the tip of the aspirating probe prior to the tip entering the liquid to be aspirated;
   moving the tip into the sample, whereby a volume of air is located between the top of the liquid and the piston of the piston pump;
   moving the piston of the piston pump a predetermined distance which corresponds to a selected volume of liquid to be aspirated, whereby a column of liquid is aspirated into the tip;
   measuring the air pressure in the volume of air when the piston stops moving and the column of sample aspirated into the tip has equilibrated ($P_{A/Dfinal}$);
   obtaining Volume/ADC, wherein ADC is pressure as expressed in analog/digital counts and Volume/ADC is the change in the volume of the gas per unit ADC;
   determining the piston volume created by the movement of the piston; and
   after aspiration determining the volume of the column of sample aspirated by the following formula:

$$V_{liquid\ aspirated} = V_{piston\ volume} - ((P_{A/Dinitial} - P_{A/Dfinal}) * \text{Volume}/ADC),$$

wherein
   $P_{A/Dinitial}$ is initial air pressure before the sample enters the tip,
   $P_{A/Dfinal}$ is final pressure of the volume of air after the column of liquid has equilibrated
   dispensing the sample into a sample holder;
   optionally dispensing a reagent into the sample holder;
   performing a measurement on the sample; and
   determining a concentration of analyte in the sample based on the measurement on the sample and the determined volume of the column of sample.

16. A method as claimed in claim 15, wherein a reagent is added to the sample holder.

17. A method as claimed in claim 15, wherein the sample holder comprises a slide, cuvette or cup-shaped well.

18. A method as claimed in claim 15 wherein the measurement on the sample is performed by a photometer, potentiometer, or luminometer.

* * * * *